Figure 1:
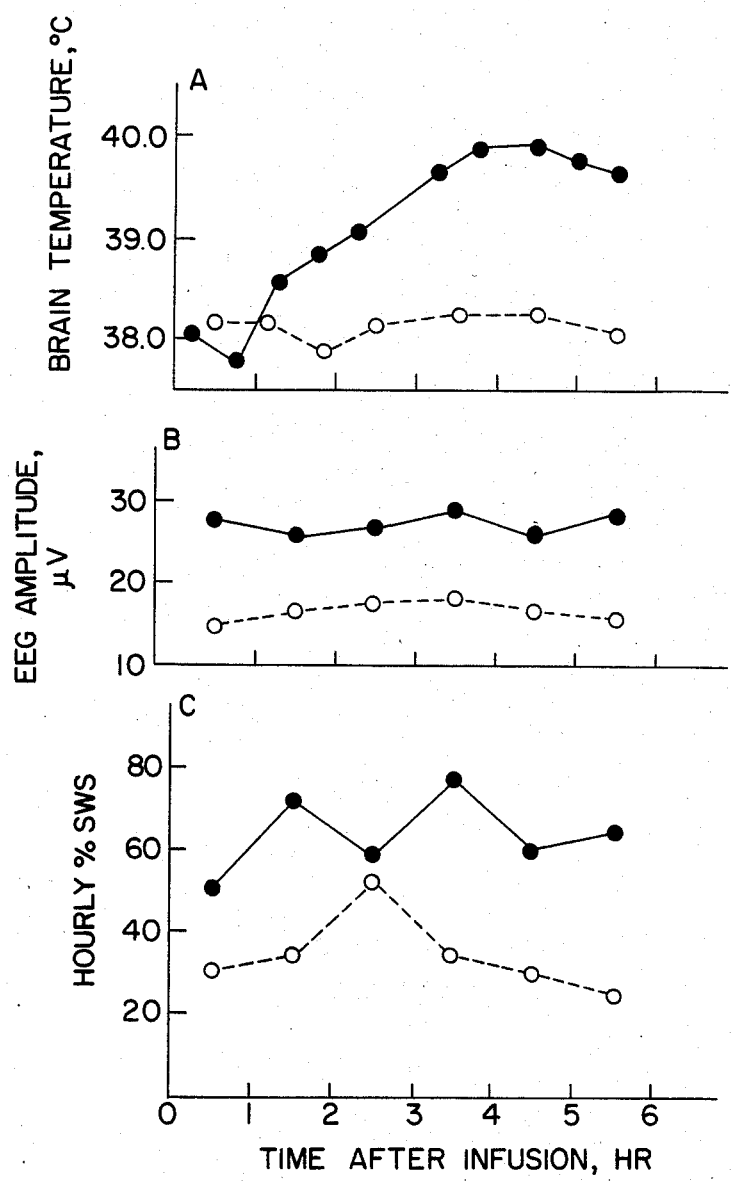

United States Patent [19]

Krueger et al.

[11] Patent Number: 4,698,330
[45] Date of Patent: Oct. 6, 1987

[54] SOMNOGENIC COMPOSITIONS AND METHOD OF USE

[75] Inventors: James M. Krueger, Highland Park, Ill.; John R. Pappenheimer; Manfred L. Karnovsky, both of Cambridge, Mass.; Pierre Lefrancier, Bures sur Yvette, France; Jean Choay; Louis Chedid, both of Paris, France; Edgar Lederer, Sceaux, France

[73] Assignee: President & Fellows of Harvard College, Cambridge, Mass.

[21] Appl. No.: 508,482

[22] Filed: Jun. 27, 1983

[51] Int. Cl.$^4$ ............................................. A61K 37/02
[52] U.S. Cl. .................................................... 514/19
[58] Field of Search ................. 260/112.5 R; 424/177; 514/19

[56] References Cited

U.S. PATENT DOCUMENTS 4,357,322  11/1982  Rooks, II et al. .................... 424/177

OTHER PUBLICATIONS

Krueger et al., *J. Exp. Med.*, 159, 68–76 (1984).
Pappenheimer et al., *J. Neurophysiol*, 38, 1299–1311 (1975).
Wexler et al., *Neurosciences Abstracts*, 8, 842 (1982).
Kotani et al., *Biken J.*, 19, 9–13 (1976).
Masek et al., *Toxicon Suppl.*, 1, 991–1003 (1978).
Krueger et al., *Am. J. Physiol.*, 238, E116–E123 (1950).
Garcia–Arraras et al., *J. Neurophysiology*, 49, 528–533 (1983).
Garcia–Arraras, *Dissertation* (Div. of Med. Sci., Harvard U. Boston), 1981.
Goodrich et al., *J. Appl. Physiol.*, 2, 137–140 (1969).
Garcia–Arraras, *Am. J. Physiol.*, 24, F269–F274, (1979).
Krueger et al., *Proc. Natl. Acad. Sci., USA*, 79, 6102–6106 (1982).
Lederer, *J. Med. Chem.*, 23, 819–925 (1980).
Lederer, *J. Med. Chem.*, 25, 87–90 (1982).
Parant et al., *J. of Infectious Diseases*, 142, No. 5, 708–715 (1980).
Krueger et al., *J. Biol. Chem.*, 257, No. 4, 1664–1669 (1982).
Ellonz et al., *Biochem. Biophyso. Res. Comm.*, 59, 1317–1325 (1974).
Riveau et al. *J. Exp. Med.* 152, 869–877 (1980).

*Primary Examiner*—Johnnie R. Brown
*Assistant Examiner*—F. T. Moezie
*Attorney, Agent, or Firm*—Weiser and Stapler

[57] ABSTRACT

Biological compositions which induce sleep of the slow-wave type which comprise biological carriers and sleep-inducing muramyl peptides such as acetylmuramyl-L-alanyl-D-isoglutamine and derivatives thereof and methods of using such compositions.

13 Claims, 5 Drawing Figures

EFFECTS OF AC MUR-ALA-IGLN-LYS ON RABBITS 9T

EFFECT OF AC-MUR-ALA-IGLN ON DURATION OF SLEEP EPISODES

EFFECTS OF AC MUR-ALA-IGLN-LYS ON SLEEP
(B) AND BRAIN TEMPERATURE (A) IN A CAT

EFFECT OF INTRAVENOUS AC MUR-ALA-IGLN ON SWS IN RABBITS

EFFECTS OF ACETAMINOPHEN (AAP) ON SOMOGENIC (B) AND PYROGENIC (A) ACTIONS OF AC MUR-ALA-IGLN

SOMNOGENIC COMPOSITIONS AND METHOD OF USE

The invention described herein was supported by grants from the American Heart Association, the Office of Naval Research and the National Institute of Health, Division of Research Resources.

This invention provides biological compositions which are sleep-promoting. More particularly, the invention provides biological compositions which induce excess sleep, especially of the slow-wave sleep type (SWS) or NREMS, as measured by electro-encephalographic (EEG) analysis.

The invention also provides a method of promoting sleep in mammals by administration of these biological compositions.

The invention also provides biological compositions which comprise 2-(2-acetamido-2-desoxy-3-O-D-glucopyranosyl)-D-propionyl-L-alanyl-D-isoglutamine (MDP) and an antipyretic. Also, the invention provides methods of use of such composition, particularly by oral administration.

The invention also provides for such compositions and method of use with N-acetyl-muramyl-L-alanyl-D-isoglutaminyl-L-lysine (MDP-lysine).

The biological compositions of the invention comprise a particular type of muramyl peptides, other than MDP and MDP-lysine which are derivatives, analogs and homologs further described below.

Physiological mechanisms of sleep have been described in the literature. See, for instance, *Harrison's Principles of Internal Medicine*, Thoen, Adams, Braunwald, Isselbacher and Petersdorf, McGraw-Hill Book Company, 8th edition, Sleep and Its Abnormalities by R. D. Adams, (pp. 122-127).

By means of electro-encephalographic analysis, five stages of sleep, associated with two alternating physiologic mechanisms, have been defined. Relaxed wakefulness is found to be accompanied by sinusoidal alpha waves of 8 to 12 cycles per second (cps) and low-voltage fast activity of mixed frequency in the EEG; there are the usual associated blinks, eye and limb movements, and moderate tone in all the skeletal muscles. As a person falls asleep and the muscles relax, the eyelids droop, the eyes begin to roll from side to side, and the EEG pattern changes to one of progressively lower voltage and mixed frequency. This is called stage I sleep. As sleep deepens into stage II, bursts of 12- to 14-cps waves (sleep spindles) and high-amplitude, sharp, slow-wave (k) complexes appear. By now eye movements have ceased, but muscle tone is maintained. The deep sleep of stages III and IV is featured by an increasing proportion of high-voltage, slow-wave activity in the EEG. In stage V, rapid eye movements return and muscle tension increases in the jaw, whereas the neck, trunk, and limb muscles, after a few quivering, tremulous, or myoclonic movements, become completely slack. The first four stages are called non-rapid eye movement sleep (NREMS); the last stage is variously designated as rapid eye movement sleep (REMS), paradoxic sleep (PS), or activated sleep (AS).

In a typical night the normal drowsy adult passes successively through stages I, II, III, and IV of NREMS. After about 70 min, mostly spent in stages III and IV, the first REMS period occurs, usually heralded by an increase in body movements and a shift in the EEG pattern from stage IV to II. This NREMS-REMS cycle (activity-rest cycle of Kleitman) is repeated at about the same interval four to six times during the night, depending on the length of sleep. The first REMS cycle may be brief, and the later cycles include less stage IV NREMS.

Another informative literature review is "Sleep Disorders", Peter Hauri, *Current Concepts*, Scope Publication 2nd Ed., 1982. An understanding of the mechanism and physiology of sleep is helpful in the better understanding of how the muramyl peptides differ from the traditional sleep-inducing drugs and their effects.

The two most important types of drugs used as sleep-inducers or sedatives in the United States are the barbiturates and the benzodiazepines, the latter being that most commonly prescribed. Flurazepam is reported to be the most widely prescribed hypnotic in North America. Solomon, White, Parron, and Mendelson, *Sleeping Pills, Insomnia and Medical Practice*, Special Report, N. Eng. J. Med. 300: 803-808, 1973.

This survey article underscores that the benzodiazepines have several serious potentially hazardous attributes, which they share with barbiturate hypnotics. The article warns of the residual daytime effects, including the effect on mood, mental alertness and visual motor co-ordination.

There is a serious need for a drug which does not have the shortcomings and side-effects of the known sleep-inducing drugs. As far as is known, there has been no drug available which promotes and simulates natural sleep. The muramyl peptides used here make a significant contribution in that direction.

Pappenheimer and colleagues purified a potent sleep factor (Factor S) from cerebrospinal fluid or from brains of sleep-deprived animals (Fencl and Pappenheimer (1971), Factors in cerebrospinal fluid from goats that affect sleep and activity in rats. *J. Physiology.*, 216, 565-589 and Reference 1). Unless cited in the text, citations are identified by numerals which are keyed to the citations in a table at the end of the text. When injected into the cerebral ventricles of rats, cats, rabbits or monkeys, it induced deep excess slow-wave sleep for 6-12 hours. Subsequently, a substance having similar somnogenic and chemical properties was isolated from human urine; this substance proved to be a muramyl peptide of molecular weight 922 (JBC, 1982). Further studies showed that certain synthetic muramyl peptides described below, also have strong somnogenic effects.

The muramyl peptides used in the invention promote a sleep which is more similar to natural sleep than sleep induced by known sleep-inducers, like the benzodiazepenes or barbiturates. An advantage of the muramyl peptides used herein is that a subject awakened from muramyl peptide-induced sleep has the normal behavior of one that has been kept awake and has not been administered a drug. This behavior differs significantly from that which takes place after arousal from sleep induced by barbiturates.

When allowed to go back to sleep, the latency to return to sleep after arousal is significantly reduced. Also the EEG slow-wave amplitude is the same as that observed when the subject is allowed to return to sleep after sleep deprivation.

An important aspect of this work is the discovery that the muramyl peptide-containing compositions do not suppress the REM sleep phase; the REM sleep phase is delayed. This is another parallel with recovery from normal sleep deprivation. See Hauri, above cited, at page 18 for a description of recovery from normal sleep deprivation.

This is a unique property of these muramyl peptides because most drugs which are commonly used as sleep-promoters (such as the barbiturates or benzodiazepines) suppress the REM phase.

Furthermore, the muramyl peptides-containing compositions did not affect the episodic nature of sleep when tested in rats, rabbits, cats and a primate, the squirrel monkey (2).

Not inhibiting the REM phase is an important property of the muramyl peptide compositions since that is the stage during which dreams occur and which tends to be depressed when using the common sleep-promoting drugs.

The muramyl peptide compositions used in the invention increase the number of episodes of SWS and the depth of the SWS as evidenced by the higher amplitude of the slow-wave component of the EEG.

As far as it is known, the muramyl peptides have a unique combination of beneficial and useful properties which the commonly used drugs for promoting sleep do not possess.

The use of the muramyl peptide compositions is generally accompanied by a pyrogenic effect in the order of 1° to 2° C. It has been noted however that the time course of the somnogenic and pyrogenic responses are different, suggesting the possibility that the somnogenic and pyrogenic effects may be dissociated from each other.

The pyrogenic effect can be suppressed without blocking the sleep-inducing and promoting effect of the muramyl peptides. The pyrogenic effect may be suppressed by the use of an appropriate, biologically acceptable antipyretic such as a salicylate, like acetyl salicylic acid (aspirin), or those of the acetaminophen or phenacetin type. For suitable antipyretics, see *Pharmacological Basis of Therapeutics*, Goodman and Gilman, McMillan Publishing Co., Inc., 5th Ed., Chapter 17, "Analgesic-Antipyretics", by Woodbury and Fingl, which is incorporated herein by reference.

With the use of the compositions of the invention, excess sleep persisting for 6 to 12 hours has been observed. In rabbits the induced excess sleep results primarily from an increase in sleep episodes lasting for more than 8 minutes.

It is known that muramic acid and diaminopimelic acid are constituents of polymeric peptidoglycans in the cell walls of bacteria and the subunits are immunostimulants and pyrogens (3). The simplest synthetic analog that has both immunostimulatory and pyrogenic effects is N-acetylmuramyl-L-alanyl-D-isoglutamine (AcMur-ala-igln, "muramyl dipeptide" (MDP)); (4) and many derivatives of this basic structure have been examined for their immunological and pyrogenic properties (3, 5, 6). The finding that the composition of sleep factor purified from brain or from urine is closely related to bacterial peptidoglycans led to an investigation of the effects of some synthetic muramyl peptides on sleep.

Muramyl peptide was first synthesized with a view to determining the simplest chemical structure capable of mimicking the immunostimulatory properties of the bacterial peptidoglycans (4). Subsequent work showed that AcMur-ala-igln and several of its derivatives are pyrogenic, although some derivatives that are immunostimulants are not pyrogens (5). The pyrogenic effects of systemically administered acMur-ala-igln may be mediated by formation of leukocytic pyrogens (7) but it is also true, as shown by Riveau et al. (8) and confirmed in the work in conjunction with the invention, that pmol doses of AcMur-ala-igln administered intraventricularly elicit long-lasting febrile responses. In thise case, AcMur-ala-igln may act directly on temperature-regulating neurons or indirectly through centrally generated endogenous pyrogens.

The state of the prior art has been discussed by Krueger, Pappenheimer and Karnovsky in "Sleep-promoting Effects of Muramyl Peptides", *Proc. Natl. Acad. Sci., USA*, vol. 79, pp. 6102–6108, October 1982. This article discusses a sleep-promoting factor derived from human urine which has recently been described by Krueger et al. (9,10) and by Garcia-Arraras and Pappenheimer (11). Correlation of amino acid and amino sugar analyses with sleep-promoting activities of purified fractions indicated that the sleep factor contained muramic acid, alanine, glutamic acid, and diaminopimelic acid. Chemical and physiological properties of the urinary factor resemble those of the sleep factor found in sterile cerebrospinal fluid and in acid/acetone extracts of brains from sleep-deprived animals (10,12). In rabbits, intraventricular infusion of 10 pmol of the pure factor induces excess slow-wave sleep (SWS) for 5–10 hr after the infusion. The effects are primarily on the duration of SWS and on the amplitude of cortical slow waves; there is relatively little effect on rapid eye movement (REM) sleep. The excess SWS appears to be normal from a behavioral point of view (13).

More recently it has been reported that MDP and MDP-lys induced sleep in rabbits and cats (2).

A comprehensive recent review of the state of the art is presented by Pappenheimer in *J. Physiol.* (1983), 336, pp. 1–11, "Induction of Sleep by Muramyl Peptides, Bayliss-Starling Memorial Lecture".

In accordance with the invention, it has been discovered that certain muramyl peptide of the class illustrated below, can mimic the sleep-promoting effects of sleep factor. The response may be modified by pyrogenic effects and by other changes of autonomic function.

Further in accordance with the invention, it has been found that AcMur-ala-igln and AcMur-ala-igln-lys are effective orally to induce excess SWS and that the pyrogenic effect caused by these compounds may be dissociated from the sleep-inducing effect.

Many of the synthetic muramyl peptides, including MDP, are pyrogenic as well as somnogenic. Thus MDP in dosage sufficient to induce excess sleep also induces a rise of 1°-2° C. in body temperature; in some species, such as cats, sleep may actually be inhibited during the chill phase of the pyrogenic effect. However, the pyrogenic effects of the synthetic muramyl peptides may be attenuated or suppressed by suitable antipyretics such as acetaminophen without altering the sleep-promoting effects. The somnogenic muramyl peptide isolated from human urine by Krueger et al. is only a weak pyrogen and may induce deep excess slow-wave sleep without change of body temperature.

It has been noted in accordance with the invention that the excess sleep induced by the class of muramyl peptides used herein, such as AcMur-ala-igln is easily disturbed by procedures such as the insertion of rectal probes for measurement of temperature or even by the presence of human activity in an open laboratory. The animals can be easily be aroused by noise or, if left to themselves, may awaken spontaneously from time to time to eat, drink and groom. Microinjection studies indicate that the site of action of the sleep factor is localized to a region between the basal forebrain and the mesodiencephalic junction.

The muramyl peptides used herein when administered intraventricularly to rabbits in doses of 75–150 pmol per rabbit cause the somnogenic effects of the urinary muramyl peptide. It has been found that the compounds of the invention are effective in very low doses. This suggests the presence in brain of receptors that have a high affinity for muramyl peptides and it can be postulated that such compounds, or some endogenous equivalent, play an important role in the physiology of sleep and temperature regulation.

The type of muramyl peptides used as sleep-inducers in accordance with the invention may be categorized in certain sub-groups. Preferred sub-groups of the MDP-type compounds are (1) the gamma-alkyl-substituted, preferably lower alkyl such as methyl, ethyl and propyl esters of Mur-NAc-L-ala-D-iso-gln;
(2) the alpha-alkyl, preferably lower alkyl such as the methyl, ethyl and propyl mono-esters of Mur-NAc-L-ala-D-glu;
(3) the alkyl, preferably lower alkyl such as the methyl, ethyl and propyl diesters of Mur-Nac-L-ala-D-glu.

Another preferred sub-group of the muramyl peptides used in the invention are those in which the second amino acid of the peptide chain is linked (through its free carboxylic function) to at least one other amino acid. Typical of such additional amino acids are lysine, tyrosine, meso-diaminopimelic acid (DAP), alanine and others. The amino acid may be in the L- or D-form. The amino acid subsequent to the second amino acid may be isoglutamine or the like.

Another preferred sub-group of the muramyl peptides used in the invention are lower alkyl, such as methyl, ethyl or propyl mono- and diesters of the longer peptides described above.

Yet another highly preferred sub-group of the compounds used in the invention are those which are constituted by more than one saccharide unit and where the N-acetylmuramic acid group (N-acetyl-Mur) is linked to an N-acetyl-D-glucosamine (N-AcGlc) by a beta (1→4) linkage. It should be noted that the N-acetyl-Mur may be N-acyl-Mur wherein acyl is glycolyl or acetyl.

Thus the compounds of the invention may be a polysaccharide, typically a disaccharide, like N-AcGlc-Ac-Mur, with a peptide chain (linked through the carboxyl group of the N-acyl-Mur) which peptide may be, as described above, a di-, tri-, tetra-, octa-, etc. peptide. Preferably, the first amino acid is L-alanine and the second is D-glutamic in which one or both carboxylic groups may be free or substituted as described above. Instead of D-glutamic acid, the muramyl peptides may contain D-aspartic as the second amino acid.

Instead of L-alanine, the first amino acid may be

| | |
|---|---|
| L-valyl, | L-lysyl, |
| L-leucyl, | L-ornithyl, |
| L-isoleucyl, | L-arginyl, |
| L-alpha-aminobutyryl, | L-histidyl, |
| L-threonyl, | L-glutamyl, |
| L-methionyl, | L-glutaminyl, |
| L-cysteinyl, | L-aspartyl, |
| L-phenylalanyl | L-asparaginyl, |
| L-tyrosyl, | L-prolyl, or |

-continued

| | |
|---|---|
| L-tryptophanyl, | L-hydroxyprolyl. |

In the muramyl peptides used, the first and second amino acid are in the D- and L-form, respectively.

Surprisingly, it has been found that whereas the compounds used in the invention as sleep-inducers may be dicarboxylic acids or diesters, they should not be diamides if the sleep-inducing property is to be retained. Conversely, a diamido compound of the type described herein (or others known) may have its sleep-promoting property activated by deamination.

In accordance with the invention, the other substituents on the N-acyl-muramyl structure are of secondary importance, and for instance, the ring may be substituted in the 6-position as is known in the prior art. The same applies to the N-acylglucosamine unit (when the compound is a disaccharide, etc.) which may have various substituents on the ring. Similarly to the above compounds, there may be used the corresponding nor-MDP, i.e. the 3-O-yl-acetyl-N-Ac-Mur-linked peptide rather than 3-O-yl-D-propionyl-N-Ac-Mur-linked, as in MDP.

The class of the compounds used according to the invention is illustrated by the following list of compounds which is representative and not inclusive:

1. NAc-Mur-L-ala-D-igln
2. NAc-Mur-L-ala-D-glu
3. NAc-Mur-L-ala-D-gln
4. NAc-Mur-L-ala-D-igln-gamma-OMe
5. NAc-Mur-L-ala-D-glu-alpha-OMe
6. NAc-Mur-L-ala-D-glu(OMe)-OMe
7. NAc-Mur-L-ala-D-igln-L-lys
8. NAc-Mur-L-ala-D-igln-L-tyr-OMe
9. NAc-Mur-L-ala-gamma-D-glu-m-DAP-D-ala-D-ala and
10. NAc-glucosaminyl-(1,4)-MDP or GlcNAc-(1,4)-MDP wherein
igln represents isoglutamine,
gln represents glutamine,
ala represents alanine,
glu represents glutamic acid,
OMe represents a carboxyl ester,
tyr represents tyrosine,
Mur represents muramyl, and
NAc represents N-acetyl.

The compounds of the invention are used in an amount effective to induce excess slow-wave type sleep in mammals.

For insomnia or other situations where it is desired to induce and promote sleep, it is contemplated that the compositions of the invention may be administered within a wide range of dosages depending on the particular subject, the particular muramyl peptide, the speed of onset, the duration of sleep sought, and numerous other parameters and variables which are normally taken into account in formulating dosages. One skilled in the pharmacological and medical arts will be able to determine the optimum dosage. It is contemplated that for intravenous administration of the muramyl peptide, a range of about 1 to 100 $\mu$g, e.g. about 25 $\mu$g per kg of body weight, and for oral administration, a range of about 1 mg to about 500 mg, e.g. 5 mg, per kg of body weight may be suitable. Thus a range from about 1 $\mu$g to 500 mg per kilogram of body weight is contemplated depending on these or other modes of administration.

The compositions are administered a short time (such as 15 to 30 minutes) before sleep is desired to be induced.

The compositions of the invention can be administered in any manner appropriate and prescribed by the physician. Administration may be by infusion, intravenous, intraperitoneally, or enterically, though for convenience the compositions will be administered orally.

The compositions of the invention are generally pyrogenic, causing a temperature rise of about 1° to 2° C. If it is desired to dissociate, inhibit or control the febrile response, administration of a conventional non-toxic antipyretic which does not inhibit normal sleep is recommended. The antipyretic may be administered at any time before sleep is induced, e.g., prior to, concurrently, or after the administration of the muramyl peptide. The compositions of the invention can include the antipyretic in the desired proportion, as for example from 0.1 to 99.9% by weight of the total composition.

It has been noted in accordance with the invention that the pyrogenic time curve and the SWS sleep curve are not concomitant and develop maxima at different time intervals.

Another significant observation made in conjunction with the work of the invention is that the compounds used do not suppress REM.

A further understanding of the invention can be had from the following non-limiting examples and illustrations.

The purity of AcMur-ala-igln and its derivatives was checked by amino acid and amino sugar analyses of unhydrolyzed and hydrolyzed (6M HCl, 100° C., 6 hr) samples using a Beckman 121 MB analyzer and by chromatographic procedure.

Surgical procedures for implantation of ventricular guide tubes and electroencephalogram (EEG)/EOG electrodes have been described (14). Calibrated glass bead thermistors (Fenwall; 1.2-mm outside diameter, 50 omega/°C.) were implanted through burr holes in frontal bone: the thermistor leads were buried in a mound of dental cement that also insulated the screw electrodes and supported a 9-pin miniature electrical connector. In some experiments, the rectal temperatures were measured at intervals by using a calibrated thermistor probe; temperatures estimated from the implanted brain thermistors were generally within 0.3° C. of simultaneously recorded rectal temperature.

New Zealand rabbits (male, 3–5 kg) or domestic cats were adapted to the infusion cages in a temperature-controlled room (21°–2° C.) on a 12:12 light/dark cycle. Intraventricular infusions or systemic injections were carried out between 0800 and 1000 hr and were followed by 6 or more hr of recording without disturbing the animals. The vehicle for intraventricular infusion was 0.3 ml of pyrogen-free artificial cerebrospinal fluid (155 mM NaCl/3 mM KCl/1.15 mM CaCl$_2$/0.96 mM MgCl$_2$) and the rate of infusion was 3–18 microliters/min in rabbits and up to 32 microliters/min in cats. Indomethacin for intravenous injection was dissolved in a small amount of EtOH and diluted with 150 mM NaHCO$_3$ to a concentration of 5 mg/ml. Acetaminophen (Sigma) was dissolved in sterile pyrogen-free saline.

EEG, electro-oculogram, and bodily movements were recorded on Grass polygraphs. The amplitude of EEG slow waves was recorded as the rms-rectified output from a 0.5- to 4-Hz bandpass filter (Bunco Electronics, Sharon, (T); the rms component was integrated and the integral was printed on tape every 2 min, thus providing an objective measure of the product of amplitude and duration of EEG slow waves. Each record was also analyzed visually for duration of SWS in rabbits and for both SWS and REM sleep in cats. The infusion and recording systems and examples of analysis of records are described in 1, 12, 15.

Effects of intraventricular infusions of AcMur-ala-igln or AcMur-ala-igln-lys on rabbits Intraventricular infusion of 75–150 pmol of AcMur-ala-igln or AcMur-ala-igln-lys increased the hourly percentage of SWS in rabbits from control values of about 40% to about 60% for 6 hr or more after the infusion. The amplitude of slow waves during episodes of SWS was increased and there was an increase of 1° to 2° C. in body temperature. The results obtained in a single experiment using AcMur-ala-igln-lys are shown in FIG. 1, and similar results obtained from 12 rabbits given either AcMur-ala-igln or AcMur-ala-igln-lys are summarized in Table 1. The somnogenic effects of AcMur-ala-igln resemble those elicited by factor S but the amount of synthetic peptide required to induce a comparable increase of SWS for 6 hr is roughly 10 times that of the natural product.

FIG. 1 shows the effects of AcMur-ala-igln-lys on rabbit 9T which illustrate in detail the 12 similar experiments summarized in Table 1: o, Control, no infusion; O after intraventricular infusion of 150 pmol of AcMur-ala-igln-lys (in 0.3 ml of artificial cerebrospinal fluid) for 20 min prior to zero time. The excess hourly % SWS (C) [64.5 plus-or-minus 40 (mean plus-or-minus SEM) versus 34.5 plus-or-minus 3.9 (control)] and the increased amplitude (evidence of deeper sleep) of EEG slow waves (B) began prior to onset of the febrile response (A). The effects of AcMur-ala-iGln and AcMur-ala-igln-lys may persist for 6–12 hr but recordings were ordinarily terminated after 6 hr.

TABLE 1

Effects of AcMur—Ala—iGln and of AcMur—Ala—iGln—Lys on sleep and brain temperature of rabbits

| Rabbit | Infusate | Dose, pmol | % SWS Control | % SWS Expt. | Amplitude* of slow wave, µV Control | Amplitude* of slow wave, µV Expt. | $\Delta T_{max}$, °C. |
|---|---|---|---|---|---|---|---|
| 62 | AcMur—Ala—iGln | 120 | 48 | 94 | 29 | 56 | ND |
| 65 |  | 120 | 43 | 69 | 28 | 42 | ND |
| 66 |  | 75 | 39 | 55 | 30 | 38 | 2.8 |
| 74 |  | 75 | 33 | 43 | 65 | 120 | 1.6 |
| 67 |  | 125 | 32 | 38 | 70 | 85 | 1.1 |
| 70 |  | 125 | 39 | 60 | 23 | 29 | 1.5 |
| 67 | AcMur—Ala—iGln—Lys | 100 | 32 | 62 | 70 | 145 | 1.7 |
| 69 |  | 150 | 32 | 51 | 38 | 54 | ND |
| 72 |  | 100 | 34 | 57 | 40 | 110 | ND |
| 76 |  | 100 | 35 | 62 | 52 | 77 | ND |
| 6T |  | 150 | 46 | 57 | 24 | 25 | 2.0 |
| 8T |  | 100 | 42 | 61 | 22 | 29 | 2.1 |

TABLE 1-continued

Effects of AcMur—Ala—iGln and of AcMur—Ala—iGln—Lys on sleep and brain temperature of rabbits

| Rabbit | Infusate | Dose, pmol | % SWS Control | % SWS Expt. | Amplitude* of slow wave, μV Control | Amplitude* of slow wave, μV Expt. | $\Delta T_{max}$, °C |
|---|---|---|---|---|---|---|---|
| 9T |  | 150 | 41 | 67 | 21 | 30 | 2.2 |
| Mean ± SEM |  |  | 38 ± 2 | 59 ± 5 | 39 ± 5 | 65 ± 11 | 1.9 ± 0.2 |

% SWS was measured during hr 2-6 after infusion. Expt., experimental; $\Delta T_{max}$, maximum increase in temperature; ND, not done.
*rms-Rectified voltage of 0.5- to 4-Hz band.

Figure 2:
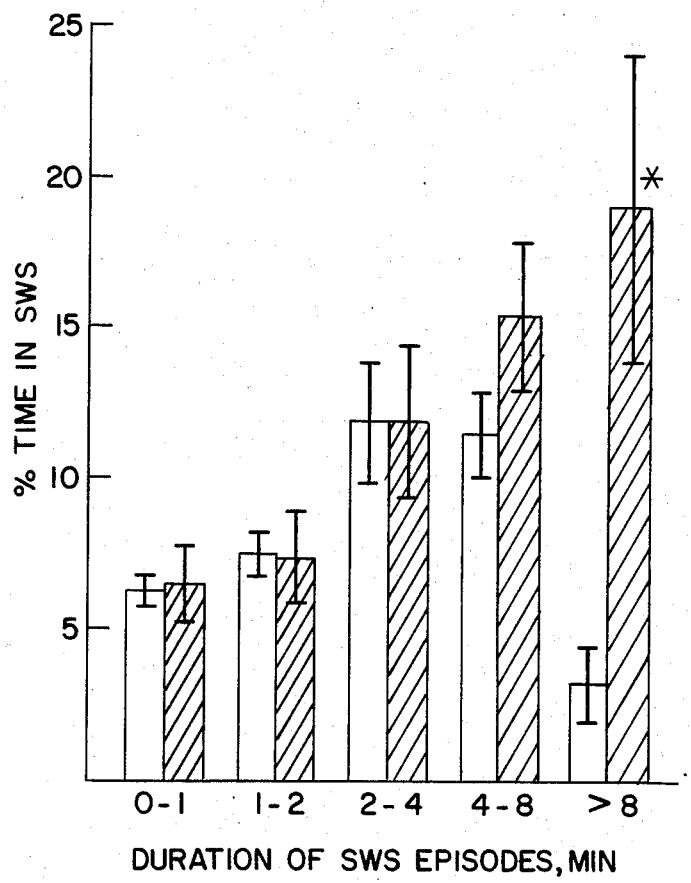

The excess sleep induced by intraventricular administration of AcMur-ala-igln or of AcMur-ala-igln-lys in rabbits appears to be normal in spite of the development of fever. The episodic nature of sleep is retained and the induced excess sleep results primarily from an increase in the number of sleep episodes lasting for more than 8 min (FIG. 2). The animals can be aroused easily and, even during maximal responses involving 80% SWS, they awaken spontaneously from time to time to eat, drink, or groom. The amplitude of slow waves during each episode was also increased (FIG. 1 and Table 1) as it is following administration of sleep factor or during the deep sleep that occurs during recovery from sleep deprivation (1).

FIG. 2 shows the effect of AcMur-ala-igln on duration of sleep episodes. The duration of each episode of SWS was defined as that period of time during which high-amplitude EEG slow waves were not interrupted for more than 15 sec by the low-amplitude EEG characteristic of wakefulness or REM. The ordinate is the percentage of time spent in SWS in each duration class in the period from hr 2 to hr 6 after administration of AcMur-ala-igln. Each value is mean plus or minus SEM of eight assays in eight rabbits. Striped bars show data after infusion of AcMur-ala-igln; open bars are data from same rabbits without infusion. The asterisk denotes a significant difference, $P<0.0125$. AcMur-ala-igln increased the number of eipsodes of SWS having durations greater than 8 min but had no significant effect on the number of episodes of SWS having durations of 1-8 min.

Figure 3:
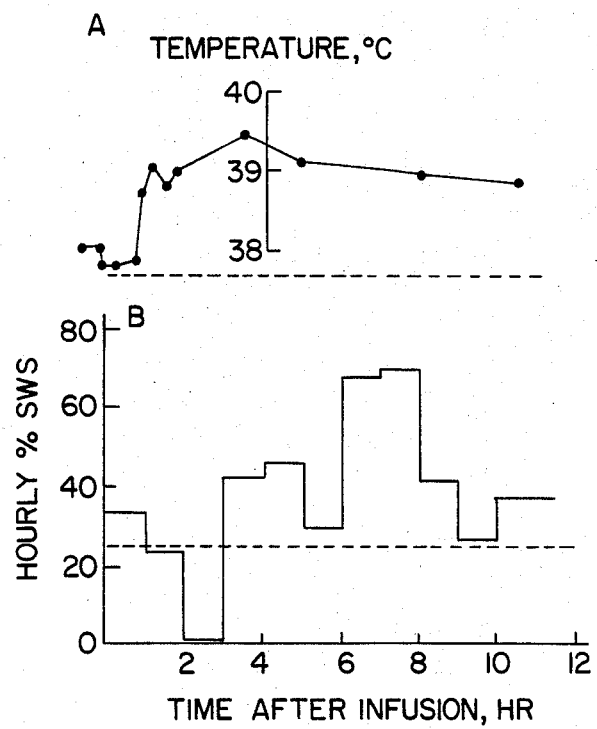

Effects of intraventricular infusions of AcMur-ala-igln or AcMur-ala-igln-Lys on Cats Each of four cats was infused intraventricularly one or more times with AcMur-ala-igln or AcMur-ala-igln-lys (200-500 pmol). The responses were more complex than those in rabbits. The febrile responses to synthetic muramyl peptides were associated with lethargy and seeming inability to enter deep (stage II) SWS for 2-4 hr after the infusion; REM sleep was completely suppressed during this period. If the investigator entered the experimental chamber during this period, the cats remained curled up in their litter boxes and did not come forward to be petted as usual. Only after the febrile response had reached its peak did the cats start to sleep for abnormally long periods in deep stage II SWS alternating with periods of REM sleep. The SWS and temperature responses of one cat to 250 pmol of AcMur-ala-igln-lys delivered intraventricularly during 15 min prior to start of recording is shown in FIG. 3. Similar results were obtained from each of the other three cats although the time courses of the febrile response and the periods of sleep suppression were variable. However, all cats receiving the synthetic muramyl peptides underwent an abnormally long period of deep SWS after the initial period of sleep suppression. A similar delay in the onset of excess SWS was noted by Garcia-Arraras (12) after infusion of natural sleep factor in cats.

FIG. 3 shows the effects of AcMur-ala-igln-lys on sleep (B) and brain temperature (A) in a cat; 240 pmol of AcMur-ala-igln-lys was infused intraventricularly during 20 min prior to zero time. Normal sleep was partially inhibited during the chill phase of the pyrogenic response (0-3 hr). REM sleep (not shown) was completely suppressed in this period. Excess SWS induced by AcMur-ala-igln-lys lasted for 3-8 hr after infusion. (A) - - - , Control=37.7 plus or minus 0.2° C. (B) - - - , Control=27 plus or minus 5%. Similar responses were observed following one or more infusions of AcMur-ala-igln or AcMur-ala-igln-lys in each of four cats.

Effects of Intravenous, Intraperitoneal, and Enteric AcMur-ala-igln

Figure 4:
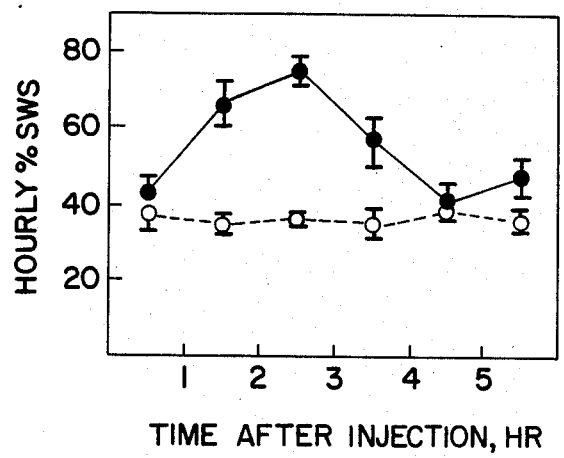

Systemic administration of AcMur-ala-igln induces a febrile response in rabbits (6, 8). The somnogenic effects can also be elicited by intravenous and intraperitoneal injection or by administration via stomach tube. The average magnitude and time course of the somnogenic effects of AcMur-ala-igln administered intravanously to rabbits in doses of 150-200 nmol/kg(75-100 μg) is shown in FIG. 4. The sleep response reaches a maximum about 3 hr after injection and returns to near control values within 5 hr. During the first 3 hr, including the period of maximum sleep, the animals appear normal in the sense that they can be aroused easily and respond to handling. after 3 to 4 hr however, the animals become unresponsive and may fail to open their eyes even when they are awake. In some animals, abnormal lacrimation, nasal secretion, and inflammation of the conjunctiva were noted. Evidently, the relatively large doses of AcMur-ala-igln required to induce pyrogenic or somnogenic effects via the intravenous route also cause disturbances of other autonomic functions. Other side effects of AcMur-ala-igln have been reviewed by Lederer (3). Masek et al (8) reported that intravenous injection of bacterial peptidoglycans or of AcMur-ala-igln can cause suppression of REM sleep in rats for several hours; it may be that, in this species, as in the cat (FIG. 3), the initial effect of AcMur-ala-igln is inhibitory.

The effect of intravenous AcMur-Ala-iGln on SWS in rabbits is shown in FIG. (4) wherein ● denotes values after a single intravanous injection of 150-200 nmol/kg at zero time; ○, control values from same rabbits. Each value is mean ±SEM of 11 assays in eight rabbits. Intravenous AcMur-ala-igln, in doses sufficient to iduce excess SWS and pyrexia, also caused deleterious side effects after about 3 hr. In contrast, much smaller doses of AcMur-ala-igln delivered intraventricularly did not cause deleterious effects and the excess SWS continued for 6-10 hr. (Compare FIGS. 4 and 1C).

In two rabbits, sleep responses were recorded after intraperitoneal injection of AcMur-ala-igln by stomach tube (5 mg/kg). Substantial sleep responses (ca. 50% increase of SWS for 6 hr) were noted in both cases.

Effects of Indomethacin and Acetaminophen

The time course of the pyrogenic response to Ac-Mur-ala-igln was sometimes quite different from that of the somnogenic response and, in some animals, the natural muramyl peptide isolated from urine induced substantial excess SWS without significant alteration of temperature. This suggests the possibility that the somnogenic effect of AcMur-ala-igln might be dissociated from its pyrogenic effect by previous treatment with antipyretics. In preliminary experiments, indomethacin was used as an antipyretic because Parant et al. (7) had shown that this drug (in doses of 40 mg/kg) was effective in blocking the pyrogenic response to intravanously administered AcMur-ala-igln. However, indomethacin alone caused toxic reactions in rabbits and cats, even in doses as low as 1 mg/kg; toxic reactions included diarrhea, lethargy, and inhibition of normal sleep. For this reason, the less toxic acetaminophen was used to suppress the pyrogenic effects of AcMur-ala-igln. The results for six rabbits injected intravanously with AcMur-ala-igln at 120 μg/kg 30 min after intravanous injection of acetaminophen at 10 mg/kg are summarized in FIG. 5. It is clear that, under these conditions a substantial somnogenic effect was obtained for 3 to 4 hr with only a weak associated febrile response. In some animals, there was no significant increase in temperature during the sleep response. After about 4 hr, the animals developed toxic reactions similar to those that follow the intravanous administration of AcMur-ala-igln alone.

Figure 5:
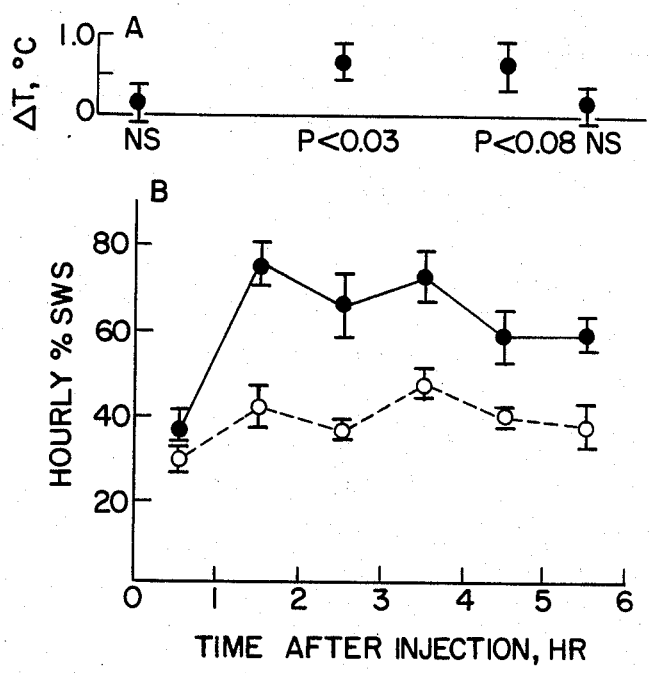

In FIG. 5, the symbols mean the following: O, AAP alone; ●, AAP followed by 120 μg of AcMur-ala-igln intravanously at time zero. Each value is mean ±SEM of six assays in six rabbits. In A, the average of the individual increases (ΔT values) in rectal temperature induced by AcMur-ala-igln together with AAP is compared with that induced by AAP alone in each of six rabbits. AAP alone had no significant effects on either sleep or rectal temperature nor did it block the sleep-inducing effects of AcMur-ala-igln [hourly % SWS: AAP alone, 41±3 (mean ±SEM); AAP together with AcMur-ala-igln, 67±3]. However, the pyrogenic effects of AcMur-ala-igln were completely or partially suppressed by AAP. The average ΔT after AcMur-ala-igln with AAP was less than 0.7° C. as compared with 1.9±0.2° C. after AcMur-ala-igln alone (Table 1) (NS, not significant).

Indomethacin did not block either the pyrogenic or the somnogenic effects of intraventricularly administered AcMur-ala-igln in 10 out of 10 trials in six rabbits. Similar results were obtained with acetaminophen in two rabbits. Likewise, aspirin causes like suppression of the febrile response. It could be an antipyretic of choice.

At present, there is no explanation for the fact that these drugs suppress the pyrogenic effects of AcMur-ala-igln when it is delivered intravanously in rabbits.

For purposes of the invention, however, it is noteworthy that the somnogenic effect of intravanously administered AcMur-ala-igln can be dissociated from its pyrogenic effect by prior treatment with an antipyretic like aspirin or acetominophen.

Administration of the anitipyretic generally takes place prior to the onset of sleep.

Effects of Some AcMur-ala-igln Derivatives

Several AcMur-ala-igln derivatives were infused intraventricularly into rabbits with a view to determining (i) relationships between structure of muramyl peptides and somnogenic activity, (ii) whether some derivatives might be found that would induce sleep without fever and other effects such as dose responses. The results are summarized in Table 2 and compared with the effects of AcMur-ala-igln and AcMur-ala-igln-lys.

TABLE 2

Somnogenic and Pyrogenic Effects of AcMur—ala—igln, and Other Compounds

| Compound | Dose nmol | # N | % SWS, 6 hr post infusion Control | % SWS, 6 hr post infusion Expt | Effect Somn | Effect Pyr | Immuno-stimulatory effect |
|---|---|---|---|---|---|---|---|
| 1. MDP, NAc—Mur—L-ala-D-igln | 0.01 | 4 | 37 ± 2 | 39 ± 4 | + | − | |
|  | 0.05 | 4 | 37 ± 2 | 49 ± 3* | + | + | |
|  | 0.1 | 6 | 40 ± 2 | 62 ± 7* | + | + | +(1) |
|  | 1.0 | 3 | 40 ± 2 | 76 ± 7* | + | + | |
|  | 10.0 | 4 | 37 ± 1 | 65 ± 6* | + | + | |
| 2. NAc—Mur—L-ala-D-glu | 0.2 | 4 | 38 ± 1 | 43 ± 3 | + | − | +(2) |
|  | 2.0 | 4 | 36 ± 3 | 51 ± 3 | + | + | |
| 3. NAc—Mur—L-ala-D-gln | 0.2 | 4 | 28–44 | 32—32 | − | − | +(2) |
|  | 2.0 | 4 | 46 ± 3 | 45 ± 1 | − | + | |
|  | 20.0 | 2 | 34–6 | 58–66 | + | + | |
| 4. NAc—Mur—L-ala-D-igln-gamma-OMe | 2.0 | 6 | 39 ± 3 | 56 ± 7* | + | + | ND |
| 5. NAc—Mur—L-ala-D-glu-alpha-OMe | 2.0 | 4 | 42 ± 4 | 72 ± 4* | + | + | ND |
|  | 0.2 | 2 | 38–40 | 47–61 | + | + | |
| 6. NAc—Mur—L-ala-D-glu(OMe)—OMe | 2.0 | 4 | 43 ± 4 | 66 ± 4* | + | + | ND |
| 7. NAc—Mur—L-ala-D-igln-L-lys | 0.13 | 5 | 35 ± 2 | 60 ± 3 | + | + | +(3) |
| 8. NAc—Mur—L-ala-D-igln-L-tyr-OMe | 0.15 | 2 | 36–44 | 68—68 | + | + | ND |
| 9. NAc—Mur—L-ala-gamma-D-glu m-DAP—D-ala-D-ala | 0.15 | 3 | 41 ± 3 | 46 ± 3 | + | − | +(4) |
|  | 0.2 | 3 | 41 ± 2 | 65 ± 5* | + | + | |
| 10. Nac—glc-1,4-MDP | 0.2 | 3 | 45 ± 3 | 60 ± 5* | + | + | |

TABLE 2-continued

Somnogenic and Pyrogenic Effects of
AcMur—ala—igln, and Other Compounds

| Compound | Dose nmol | # N | % SWS, 6 hr post infusion Control | % SWS, 6 hr post infusion Expt | Effect Somn | Effect Pyr | Immunostimulatory effect |
|---|---|---|---|---|---|---|---|
| 11. NAc—Mur—D-ala-D-igln | 0.5 | 3 | 33 ± 1 | 35 ± 2 | — | — | —(2) |
|  | 1.0 | 3 | 33 ± 1 | 35 ± 2 | — | — |  |
| 12. NAc—Mur—L-ala-L-igln | 0.2 | 4 | 38 ± 2 | 38 ± 4 | — | — | —(4) |
| 13. NAc—Mur—L-ala-D-gln-alpha OMe** | 0.5 | 2 | 34–42 | 31–45 | — | — | +(2) |
| 14. NAc—Mur—L-ala-D-gln-n-Bu ester | 0.25 | 2 | 37–42 | 41–47 | — | + | +(2) |
| 15. NAc—Mur—(N—Me)—L-ala-D-igln | 0.2 | 2 | 37–42 | 32–47 | — | + | +(2) |
| 16. Periodate-cleaved NAc—Mur—L-ala-D-igln[x] | 0.2 | 2 | 40–44 | 38–42 | — | — | ND |
| 17. NAc—Mur—L-ala-D-glu(NH$_2$)—NH$_2$ | 2.0 | 3 | 42 ± 3 | 43 ± 1 | — | — | ND |

% SWS was measured during hr 2-6 after infusion. Results are mean = SEM or ranges for n rabbits; ND, not done.
[x]MDP was treated with periodate to remove two carbon atoms from the muramic acid ring. One hundred nmol of MDP was incubated with 0.18 M Na metaperiodate in a volume of 40 µl overnight at 3° C. The next day 4 µl of ethylene glycol was added at room temperature. This solution was kept in the dark for 30 min and then applied to a 19-ml G-10 Sephadex column equilibrated and developed in 50 mM acetic acid. The void volume of 6 ml was discarded, the next 5.5 ml was saved. Aliquots from this fraction were subjected to amino acid analyses before and after acid hydrolysis. The amount of glu released by hydrolysis was used to calculate the dose.
*Significantly different from control ($p < 0.05$)
**Dosage 0.16 to 0.33 mg/kg, intravenously to 4 rabbits.
"Som indicates somnogenic" "Pyr", pyrogenic. a "+" in the pyrogenic column indicates more than 0.5° C. change; a "—" indicates no change.

As is shown above, the steroisomers of AcMur-ala-igln (D-D and L-L) are nonpyrogenic and they failed to induce sleep; they are also ineffective as immunostimulants even in high concentrations.

The methyl and n-butyl esters and the N-Me derivative of AcMur-ala-igln are immunostimulants but they have no pyrogenic or somnogenic effects. Similar results were obtained after intravenous injection of 500 ug of the methylated derivatives. The muramyl moiety of AcMur-ala-igln was cleaved by gentle periodate oxidation to remove carbons 5 and 6 from the glucosamine ring. This treatment abolished the somnogenic effect, indicating that the muramyl component plays an essential role in the biological activity. However, N-acetylmuramic acid by itself had no effect on sleep.

In accordance with the invention, these compounds may also be administered in conjunction with other compounds which are recommended in the treatment of insomnia and other situations where sleep inducement is indicated.

The present invention also relates to biological, including pharmacological preparations which contain the somnogenic derivatives. The pharmacological preparations according the the invention are those intended for enteral, such as oral or rectal, or parenteral administration to warm-blooded animals and which contain the pharmacological active substance as the sole ingredient or together with a pharmacologically acceptable carrier.

Tablets (100) were prepared containing 350 mg of muramyl peptide and 70 mg of an antipyretic agent.

| N—AcMur—L-ala—D-igln—1-tyr—OMe | 350 mg. |
|---|---|
| Aspirin | 70 mg. |
| Mannitol | 1200 g. |

-continued

| Cornstarch | 65 g. |
|---|---|
| Fructose | 4 g. |
| Flavor (dry powder) | 2 g. |
| Magnesium stearate | 20 g. |

The muramyl peptide and the aspirin are mixed with mannitol and granulated with a solution of the fructose and the soluble starch in 1.2 liters of water. The granulate is dried and subsequently screened through a screen with a mesh size of 0.5 mm. The granulate is then mixed with the remainder of the compounds, and the mixture is pressed into tablets of 1.165 g. using a 15 mm. disk and a flat bevel-edged die.

Following the procedure of the Example, but in lieu of aspirin, there may be utilized with the active muramyl peptide other known appropriate antipyretic compounds including acetaminophen, indomethacin, indole or indene acetic acids, such as Sulindac; substituted phenyl alkanoic acids, such as Ibuprofen, Ketoprofen, Nasproxen, Fenoprofen, Alcofenac, and the like; N-Aryl anthranilic acids, such as Flufenamic, Meclofenamic and the like; aspirin-like and acetaminophen-like compounds. The amount of antipyretic compound in the composition may vary according to the antipyretic effect desired.

Similarly any one of the aforementioned active muramyl peptides may be used either together with N-AcMur-L-ala-D-igln-L-tyrOMe or in substitution therefore. Of particular interest were the compositions and the mixtures with NAc-Mur-L-ala-D-glu-alpha-OMe, NAc-Mur-L-ala-D-igln-L-lys, and NAc-Mur-L-ala-gamma-D-glu-m-DAP-D-ala-D-ala and an antipyretic. Of particular interest is the composition with NAc-glc-1,4-MDP alone or with an antipyretic.

The novel biological and pharmaceutical preparations contain about 0.1% to about 99.9%, preferably from 20% to about 90% of the active substance. Pharmaceutical preparations according to the invention can be in dosage unit form, such as coated tablets, tablets, capsules, suppositories or ampoules.

The biologically active or pharmaceutical preparations of the present invention are prepared in a manner known per se, for example by means of conventional mixing, granulating, coating, dissolving or lyophilising methods. For example, pharmaceutical preparations for oral use can be obtained by combining the active substance with solid excipients, granulating the resulting mixture, if desired or required after addition of suitable adjuncts, to tablets or to cores for sugar-coated tablets.

Suitable excipients are, in particular, fillers, binders and/or disintegrators known to those skilled in the art. Cores for sugar-coated tablets are provided with suitable coatings, which may be resistant to gastric juices, using coatings resistant to gastric juices which are well known to those skilled in the art.

Further pharmaceutical preparations which can be used orally are dry-filled capsules made from gelatin, as well as soft-sealed capsules made from gelatin and a plasticiser such as glycerol or sorbitol. The dry-filled capsules can contain the active ingredient in the form of granules for example in admixture with fillers such as lactose binders such as starches, and/or glidants, such as talc or magnesium stearate, with or without the presence of stabilisers. In soft capsules, the active ingredient is preferably dissolved or suspended in suitable liquids, such as fatty oils, paraffin oil or liquid polyethylene glyols to which again, stabilisers can be added.

Suitable compositions for parenteral administration are, in particular, aqueous solutions of an active ingredient in a water-soluble form, and also suspensions of the active ingredient, such as corresponding oily injection, for which suitable lipophilic solvents or vehicles, such as fatty oils, for example, sesame oil, or synthetic fatty acid esters, for example ethyl oleate or triglycerides, are used, or aqueous injection suspensions which contain viscosity-increasing materials for example sodium carboxymethylcellulose, sorbitol and/or destran, with or without stabilisers. Liposome compositions may be suitable.

TABLE OF REFERENCES

1. Pappenheimer, J. R., Koski, G., Fencl, V., Karnovsky, M. I., & Krueger, J. M. (1975) *J. Neurophysiol* 38, 1299-1311
2. Wxler, Harling and Moore-Ede, Muramyl Dipeptide Induces Sleep, *Neurosciences Abstracts,* vol. 8, p. 842 (1982).
   The abstract reports that the Administration of MDP induces non-REM but not REM sleep in the squirrel monkey, and causes an increase of NREM sleep throughout the subjective day. The timing of the circadian temperature and sleep-wake cycles does not appear to be altered on the day after administration of MDP.
3. Lederer, E. (1980); *J. Med. Chem.* 23, 819-925.
4. Ellouz, F., Adam, A. Ciorbaru, R. & Lederer, F. (1974), *Biochem. Biophys. Res. Commun.* 59, 1317-1325.
5. LeFrancier, P., Derrier, M., Jamet, X., Choay, J., Lederer, E. Audibert, F., Pasrant, M. Parant, F. & Chedid, L. (1982) *Med. Chm.* 25, 87-90.
6. Kotani, S., Watanabe, Y., Harada, K., Shiba, T., Kusomoto, S., Yokugawa, K. & Taniguchi, M. (976) *Biken J.* 19, 9-13.
7. Parant, M., Riveau, G., Parant, F., Dinarello, C. A., Wolff, S. M., & Chedid, L. (1980) *J. Infect. Dis* 142, 708-715.
8. Masek, K., Kadlecova, O. & Petrovicky, P. (1978) *Toxicon Suppl* 1, 991-1003.
9. Krueger, J. M., Bascik, J. & Garcia-Arraras, J. (1950), *Am J. Physiol* 238, E116-E123.
10. Krueger, J. M., Pappenheimer, J. R. & Karnovsky, M. I. (February, 1982) *J. Biol. Chem* 257, 1664-1669.
11. Garcia-Arraras and Pappenheimer, (1983) Site of action of Sleep-Inducing Muramyl Peptide Isolated from Human Urine: Micro injection Studies in Rabbit Brains, *J. Neurophysiol.* 49, 528-533.
12. Garcia-Arraras, J. E. (1981) Dissertation (Division of Medical Sciences, Harvard University, Boston).
13. Goodrich, C. A., Greehey, B., Miller, T. B. & Pappenheimer, J. R., *J. Appl. Physiol.* 2, 137-140.
14. Garcia-Arraras, J. E. (1979) *Am. J. Physiol* 24, F269-F274.
15. Riveau, G., Masek, K., Parant, M., & Chedid, L. (1980) J. Exp. Med. 152, 869-877.

We claim:

1. A method for inducing natural sleep of the slow-wave type in a primate which comprises administering orally to a primate in need thereof in an amount sufficient to induce sleep of the slow-wave type, a biological somnogenic composition which comprises a biologically acceptable carrier, and a sleep-inducing muramyl peptide selected from the following;
   (1) N-acetylmuramyl-L-alanyl-D-glutamic acid,
   (2) N-acetylmuramyl-L-alanyl-D-glutamine,
   (3) N-acetylmuramyl-L-alanyl-D-gamma methoxy isoglutamine,
   (4) N-acetylmuramyl-L-alanyl-D-alpha methoxy glutamic acid,
   (5) N-acetylmuramyl-L-alanyl-D-alpha, gamma dimethoxy glutamic acid,
   (6) N-acetylmuramyl-L-alanyl-D-isoglutamyl-L-methoxytyrosine,
   (7) N-acetylmuramyl-L-alanyl-gamma-D-glutamyl meso diaminopimelic-D-alanyl-D-alanine,
   (8) N-acetyl-glucosaminyl-(1,4)-N-acetyl muramyl-L-alanyl-D-isoglutamine,
   inducing sleep of the slow-wave type while retaining the REM and NREM episodic nature of natural sleep, and increasing the number of sleep episodes in said primate.
2. The method of claim 1 wherein the sleep duration lasts from 4 to 6 hours.
3. The method of claim 1 which comprises administering in an antipyretic amount, an antipyretic in conjunction with said biological composition.
4. The method of claim 3 wherein the antipyretic is acetaminophen or aspirin.
5. The method of claim 3 wherein the amount of the antipyretic is an amount sufficient to control a rise in temperature.
6. The method of claim 1 wherein the composition comprises the muramyl peptide in the amount of from about 1 mg to about 500 mg.
7. The method of claim 1 wherein the muramyl peptide is N-acetyl-L-alanyl-D-glutamic acid.

8. The method of claim 1 wherein the muramyl peptide is N-acetylmuramyl-L-alanyl-D-gamma methoxy isoglutamine.

9. The method of claim 1 wherein the muramyl peptide is N-acetylmuramyl-L-alanyl-D-alpha methoxy glutamic acid.

10. The method of claim 1 wherein the muramyl peptide is N-acetylmuramyl-L-alanyl-D-alpha, gamma dimethoxy glutamic acid.

11. The method of claim 1 wherein the muramyl peptide is N-acetylmuramyl-L-alanyl-D-isoglutamyl-L-methoxy-tyrosine.

12. The method of claim 1 wherein the muramyl peptide is N-acetylmuramyl-L-alanyl-gamma-D-glutamyl meso diaminopimelic-D-alanyl-D-alanine.

13. The method of claim 1 wherein the muramyl peptide is N-acetyl-glucosaminyl-(1,4)-N-acetyl muramyl-L-alanyl-D-isoglutamine.

* * * * *